US010059728B2

(12) United States Patent
Briers et al.

(10) Patent No.: US 10,059,728 B2
(45) Date of Patent: Aug. 28, 2018

(54) METHOD FOR THE PREPARATION OF FUNCTIONALIZED CYCLOSILOXANES

(71) Applicant: Henkel AG & Co. KGaA, Duesseldorf (DE)

(72) Inventors: David Briers, Hasselt (BE); Johann Klein, Duesseldorf (DE); Esteban Mejia, Rostock (DE); Udo Kragl, Kritzmow (DE); Ralf Dunekake, Duesseldorf (DE); Marleen Winterberg, Rostock (DE); Jens Baumgard, Rostock (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/294,920

(22) Filed: Oct. 17, 2016

(65) Prior Publication Data

US 2017/0096438 A1    Apr. 6, 2017

Related U.S. Application Data

(63) Continuation of application No. PCT/EP2015/058638, filed on Apr. 22, 2015.

(30) Foreign Application Priority Data

Apr. 23, 2014   (EP) .................................... 14165544

(51) Int. Cl.
*C07F 7/00* (2006.01)
*C07F 7/21* (2006.01)

(52) U.S. Cl.
CPC ...................... *C07F 7/21* (2013.01)

(58) Field of Classification Search
CPC ........................................................ C07F 7/21
USPC ....................................................... 556/443
See application file for complete search history.

(56) References Cited

U.S. PATENT DOCUMENTS

| | | | |
|---|---|---|---|
| 2,762,829 A | 9/1956 | Kratzer et al. | |
| 2,785,147 A | 3/1957 | Kantor | |
| 2,793,222 A | 5/1957 | Kantor et al. | |
| 5,466,768 A * | 11/1995 | Yang ...................... | A61L 27/18 525/479 |
| 8,501,893 B2 | 8/2013 | Janvikul et al. | |
| 2004/0037791 A1 | 2/2004 | Richard et al. | |
| 2005/0267253 A1 | 12/2005 | Hayashi | |
| 2009/0192282 A1 | 7/2009 | Janvikul et al. | |

FOREIGN PATENT DOCUMENTS

| | | |
|---|---|---|
| JP | H0517486 A | 1/1993 |
| JP | 2004256494 A | 9/2004 |

OTHER PUBLICATIONS

Anderson Roy et al: Silicon Compounds, Silicon Compounds: Silanes and Silicones, Gelest Inc., Morrisville, PA, US, 2004, pp. 215-386.
Berthon-Gelloz G et al: "Highly beta-(E)-Selective Hydrosilylation of Terminal and Internal Alkynes Catalyzed by a (IPr) Pt(diene) Complex", The Journal of Organic Chemistry, vol. 73, No. 11, Jun. 6, 2008, pp. 4190-4197.
Andrianov K. A. et al: Synthesis of bicyclic organosilicon compounds with an ethylene bridge between the rings, Bulletin of the Academy of Sciences of the USSR; Division of Chemical Sciences, vol. 16, No. 6, Jun. 1967 (Jun. 1967), pp. 1223-1226.
F. Alonso, R. Buitrago, Y. Moglie, J. Ruiz-Martinez, A. Sepulveda-Escribano, M. Yus, Journal of Organometallic Chemistry 2011, 696,368-372.
C. Zhang, R. M. Laine, Journal of the American Chemical Society 2000, 122, 6979-6988.
B. Marciniec, M. Lewandowski, E. Bijpost, E. Malecka, M. Kubicki, E. Walcuz-Grusciora, Organometallics 1999, 18, 3968-3975.
V. Gevorgyan, L. Borisova, J. Popelis, E. Lukevics, Z. Foltynowicsz, J. Gulinski, B. Marciniec, Journal of Organometallic Chemistry 1992, 424, 15-22.
International Search Report for International PCT Patent Application No. PCT/EP2015/058638 dated Jun. 18, 2015.

* cited by examiner

*Primary Examiner* — Clinton Brooks
*Assistant Examiner* — Kofi Adzamli
(74) *Attorney, Agent, or Firm* — James E. Piotrowski

(57) ABSTRACT

The present invention relates to a method for preparing functionalized cyclosiloxanes of Formula I,

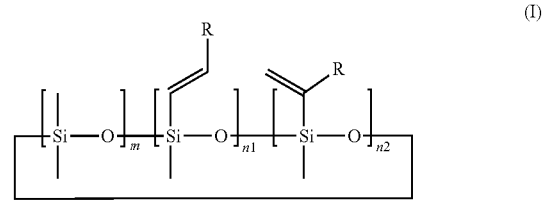

(I)

wherein R, $R^1$, $R^2$, m, n1 and n2 are as defined herein, comprising reacting (i) a cyclosiloxane of Formula II

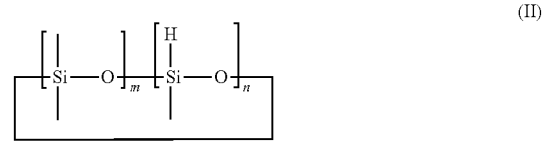

(II)

with (ii) a substituted acetylene of Formula III

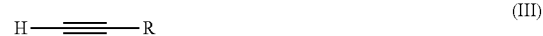

(III)

in the presence of a hydrosilylation catalyst. The invention further relates to methods for preparing biscyclosiloxanes by reacting the vinyl cyclosiloxanes obtained according to the described methods and the (bis)cyclosiloxanes obtainable according to the described methods.

12 Claims, 4 Drawing Sheets

METHOD FOR THE PREPARATION OF FUNCTIONALIZED CYCLOSILOXANES

The present invention relates to a method for preparing functionalized cyclosiloxanes and the thus prepared cyclosiloxanes.

Cyclosiloxanes are widely used as starting materials for the synthesis of poly(organo)siloxanes, which are, for example, used in cosmetics, detergents, sealants and the like, and owe their characteristic properties to the very flexible Si—O bonds, the partially ionic backbone, its water repellence and low surface tension.

Among the functionalized cyclosiloxanes, perhaps the more popular are the vinyl derivatives which are commonly used as silane coupling reagents. Nevertheless, vinyl cyclosiloxanes bearing functional groups are scarce. Although vinyl cyclosiloxane derivatives bearing aromatic rings are known, the existing methods for their synthesis are hampered by low yields. Accordingly, there exists need in the art for alternative methods for the synthesis of vinyl cyclosiloxanes that provide for higher yields.

The invention meets this need by providing a process for the synthesis of functionalized vinyl cyclosiloxane derivatives by hydrosilylation of acetylene derivatives with cyclic siloxanes that addresses the inclusion of functional groups in such cyclic monomers and the introduction of carbon-carbon bridges between cyclosiloxane monomers. Such bridged or functionalized cyclosiloxanes can be used to introduce carbon-carbon bridges or functional groups into polysiloxanes via ring opening polymerization either neat or with other cyclosiloxanes with the general formula $D_n D^H_m$ (where n and m are integer numbers, in a way that $2<n+m<11$). The functional groups, selectively introduced by this methodology can be exploited as cross-linking moieties, as anchoring points for further polymer chains (leading to grafted copolymers), or simply to modify the chemical, physical or rheological properties of the materials, for example viscosity, flexibility, permeability and/or thermal stability.

In a first aspect, the present invention therefore relates to a method of preparing a cyclosiloxane of Formula I,

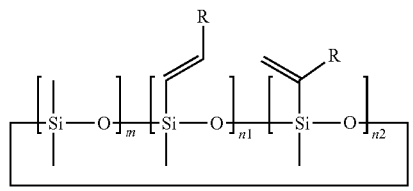

(I)

wherein each R is independently selected from the group consisting of hydrogen and an organic functionality, preferably selected from the group consisting of substituted or unsubstituted $C_{1-28}$ alkyl, $C_{2-28}$ alkenyl, $C_{2-22}$ alkynyl, $C_{3-12}$ cycloalkyl, $C_{3-12}$ cycloalkenyl, $C_{6-20}$ aryl, $C_{3-20}$ heteroaryl, preferably with 1 to 5 ring heteroatoms selected from N, O and S, $C_{7-9}$ aralkyl or alkylaryl, $C_{1-20}$ heteroalkyl, preferably with 1 to 5 heteroatoms selected from N, O, halogen and S, $C_{1-20}$ heterocyclyl with 1 to 5 ring heteroatoms selected from N, O and S, halogen, cyano, nitro, —$OR^1$, —$C(O)R^1$, —$C(O)OR^1$, —$OC(O)R^1$, —$NR^1R^2$, —$C(O)NR^1R^2$, —$NR^2C(O)R^1$, and —$Si(R^1)_o(OR^2)_{3-o}$;

$R^1$ and $R^2$ are independently selected from the group consisting of hydrogen and $C_{1-28}$ alkyl, $C_{2-28}$ alkenyl, $C_{2-22}$ alkynyl, $C_{3-12}$ cycloalkyl, $C_{3-12}$ cycloalkenyl, $C_{6-20}$ aryl, $C_{3-20}$ heteroaryl, preferably with 1 to 5 ring heteroatoms selected from N, O and S, $C_{7-9}$ aralkyl or alkylaryl, $C_{1-20}$ heteroalkyl, preferably with 1 to 5 heteroatoms selected from N, O, halogen and S, $C_{1-20}$ heterocyclyl with 1 to 5 ring heteroatoms selected from N, O and S;

each of m, n1 and n2 is 0 or an integer independently selected from 1 to 10, with m+n1+n2=3 to 10 and provided that not both of n1 and n2 are 0; and o is 0, 1, 2, or 3;

the method comprising:

reacting (i) a cyclosiloxane of Formula II

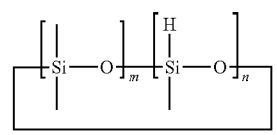

(II)

wherein m is as defined above and n=n1+n2;

with (ii) a substituted acetylene of Formula III

(III)

wherein R is as defined above in the presence of a hydrosilylation catalyst to form the cyclosiloxane of Formula I.

In a second aspect, the invention relates to a method of preparing a biscyclosiloxane of Formula IV

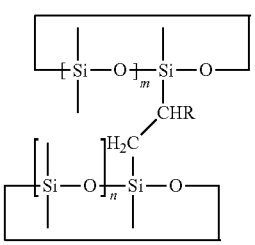

(IV)

or Formula V

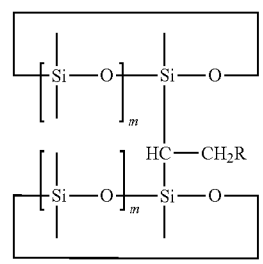

(V)

wherein each R is independently selected from the group consisting of hydrogen and an organic functionality, preferably selected from the group consisting of substituted or unsubstituted $C_{1-28}$ alkyl, $C_{2-28}$ alkenyl, $C_{2-22}$ alkynyl, $C_{3-12}$ cycloalkyl, $C_{3-12}$ cycloalkenyl, $C_{6-20}$ aryl, $C_{3-20}$ heteroaryl, preferably with 1 to 5 ring heteroatoms selected from N, O and S, $C_{7-9}$ aralkyl or alkylaryl, $C_{1-20}$ heteroalkyl, preferably with 1 to 5 heteroatoms selected from N, O, halogen and S, $C_{1-20}$ heterocyclyl with 1 to 5 ring heteroatoms selected from N, O and S, halogen, cyano, nitro, —$OR^1$, —$C(O)R^1$, —$C(O)OR^1$, —$OC(O)R^1$, —$NR^1R^2$, —$C(O)NR^1R^2$, —$NR^2C(O)R^1$, and —$Si(R^1)_o(OR^2)_{3-o}$, preferably H;

$R^1$ and $R^2$ are independently selected from the group consisting of hydrogen and $C_{1-28}$ alkyl, $C_{2-28}$ alkenyl, $C_{2-22}$ alkynyl, $C_{3-12}$ cycloalkyl, $C_{3-12}$ cycloalkenyl, $C_{6-20}$ aryl, $C_{3-20}$ heteroaryl, preferably with 1 to 5 ring heteroatoms selected from N, O and S, $C_{7-9}$ aralkyl or alkylaryl, $C_{1-20}$ heteroalkyl, preferably with 1 to 5 heteroatoms selected from N, O, halogen and S, $C_{1-20}$ heterocyclyl with 1 to 5 ring heteroatoms selected from N, O and S;

m is an integer from 2 to 9, preferably 3; and
o is 0, 1, 2, or 3;
the method comprising:
(A) reacting (i) a cyclosiloxane of Formula I

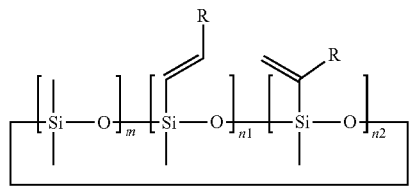

wherein R is as defined above, m is an integer of 2 to 9, preferably 3, and either (a) n1=1 and n2=0, or (b) n1=0 and n2=1, or (c) a mixture of both regioisomers (a) and (b); with (ii) a cyclosiloxane of Formula II

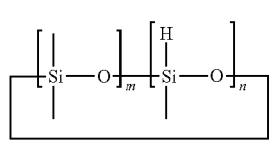

(II)

wherein m is an integer of 2 to 9, preferably 3, and n is 1; in the presence of a hydrosilylation catalyst to form the biscyclosiloxane of Formula IV or V; or
(B) reacting (i) two cyclosiloxanes of Formula II

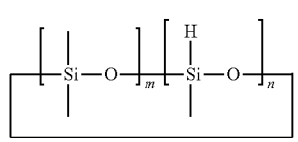

(II)

wherein m is an integer of 2 to 9, preferably 3, and n is 1; with (ii) a substituted acetylene of Formula III

(III)

wherein R is as defined above;
in the presence of a hydrosilylation catalyst to form the biscyclosiloxane of Formula IV or V.

In a still further aspect, the invention also encompasses the cyclosiloxanes obtainable according to the methods described herein.

In the cyclosiloxane of Formula I, each R is independently selected from the group consisting of hydrogen and an organic functionality. The organic functionality can comprise any functional group or hydrocarbon moiety, the latter preferably with 1 to 30 carbon atoms. In various embodiments, the organic functionality may be selected from the group consisting of substituted or unsubstituted $C_{1-28}$ alkyl, $C_{2-28}$ alkenyl, $C_{2-22}$ alkynyl, $C_{3-12}$ cycloalkyl, $C_{3-12}$ cycloalkenyl, $C_{6-20}$ aryl, $C_{3-20}$ heteroaryl, preferably with 1 to 5 ring heteroatoms selected from N, O and S, $C_{7-9}$ aralkyl or alkylaryl, $C_{1-20}$ heteroalkyl, preferably with 1 to 5 heteroatoms selected from N, O, halogen and S, $C_{1-20}$ heterocyclyl with 1 to 5 ring heteroatoms selected from N, O and S, halogen, cyano, nitro, —$OR^1$, —$C(O)R^1$, —$C(O)OR^1$, —$OC(O)R^1$, —$NR^1R^2$, —$C(O)NR^1R^2$, —$NR^2C(O)R^1$, and —$Si(R^1)_o(OR^2)_{3-o}$. Therein, $R^1$ and $R^2$ are independently selected from the group consisting of hydrogen and $C_{1-28}$ alkyl, $C_{2-28}$ alkenyl, $C_{2-22}$ alkynyl, $C_{3-12}$ cycloalkyl, $C_{3-12}$ cycloalkenyl, $C_{6-20}$ aryl, $C_{3-20}$ heteroaryl, preferably with 1 to 5 ring heteroatoms selected from N, O and S, $C_{7-9}$ aralkyl or alkylaryl, $C_{1-20}$ heteroalkyl, preferably with 1 to 5 heteroatoms selected from N, O, halogen and S, $C_{1-20}$ heterocyclyl with 1 to 5 ring heteroatoms selected from N, O and S, and o is 0, 1, 2, or 3.

When the above-listed groups are substituted, the substituent may be one or more groups independently selected from the group consisting of $C_{1-4}$ alkyl, $C_{1-4}$ haloalkyl, $C_{1-4}$ alkoxy, —$OR^1$, —$C(O)R^1$, —$C(O)OR^1$, —$OC(O)R^1$, —$NR^1R^2$, —$C(O)NR^1R^2$, —$NR^2C(O)R^1$, —$Si(R^1)_o(OR^2)_{3-o}$, —$SR^1$, —$SO_2R^1$, halogen, cyano, and nitro.

The alkyl radicals are, for example, straight-chain or branched alkyl radicals, such as methyl, ethyl, n-propyl, isopropyl, n-butyl, sec-butyl, isobutyl, tert-butyl or straight-chain or branched pentyl, hexyl, heptyl or octyl. Preference is given to $C_{1-12}$ alkyl radicals, especially $C_{1-8}$ alkyl radicals and preferably $C_{1-4}$ alkyl radicals. The mentioned alkyl radicals may be unsubstituted or substituted, e.g. by hydroxy, carboxy, $C_{1-4}$ alkoxy, especially by hydroxy.

Aryl is preferably substituted or unsubstituted $C_{6-14}$ aryl, more preferably phenyl or naphthyl, with the potential substituents being those defined above. $C_{3-20}$ heteroaryl relates to aromatic ring systems with 3 to 20 carbon atoms and one or more hetero ring atoms, preferably 1 to 5 hetero ring atoms selected from N, O and S. Exemplary heteroaryls are, without limitation, pyridine or pyrimidine.

Halogen is preferably chlorine, bromine or fluorine, with special preference being given to fluorine.

$C_{3-12}$ cycloalkyl refers to saturated cyclic hydrocarbons. $C_{3-12}$ cycloalkyl is for example cyclopropyl, cyclobutyl, cyclopentyl, cyclohexyl, trimethylcyclohexyl, menthyl, thujyl, bornyl, 1-adamantyl oder 2-adamantyl.

$C_{2-28}$ alkenyl is for example vinyl, allyl, 2-propen-2-yl, 2-buten-1-yl, 3-buten-1-yl, 1,3-butadien-2-yl, 2-penten-1-yl, 3-penten-2-yl, 2-methyl-1-buten-3-yl, 2-methyl-3-buten-2-yl, 3-methyl-2-buten-1-yl, 1,4-pentadien-3-yl, or signifies different isomers of hexenyl, octenyl, nonenyl, decenyl or dodecenyl.

$C_{3-12}$ cycloalkenyl refers to unsaturated cyclic hydrocarbon residues containing one or multiple double bonds such as 2-cyclobuten-1-yl, 2-cyclopenten-1-yl, 2-cyclohexen-1-yl, 3-cyclohexen-1-yl, 2,4-cyclohexadien-1-yl, 1-p-menthen-8-yl, 4(10)-thujen-10-yl, 2-norbornen-1-yl, 2,5-norbornadien-1-yl or 7,7-dimethyl-2,4-norcaradien-3-yl.

C$_{7-9}$ aralkyl is for example benzyl, 2-phenyl-ethyl, 1,1-dimethylbenzyl.

C$_{1-20}$ heterocyclyl relates to a saturated or unsaturated cyclic hydrocarbon residue containing one or more hetero ring atoms, preferably 1 to 5 hetero ring atoms selected from N, O and S.

—OR$^1$ can preferably be hydroxy or —O-alkyl, with alkyl being as defined above.

—C(O)R$^1$ can preferably be an aldehyde group or a keto group of the formula —C(O)-alkyl, with alkyl being as defined above.

—C(O)OR$^1$ can preferably be carboxyl —COOH or carboxylic acid ester of the formula —C(O)O-alkyl, with alkyl being as defined above.

—OC(O)R$^1$ can preferably be —OC(O)-alkyl, with alkyl being as defined above.

—Si(R$^1$)$_o$(OR$^2$)$_{3-o}$ can preferably be trialkoxysilyl, alkyldialkoxysilyl or dialkylalkoxysilyl, for example trimethoxysilyl, methyldimethoxysilyl or dimethylmethoxysilyl.

The reaction scheme for the reaction of the cyclosiloxane of Formula II with the functionalized acetylene of Formula III (2a-f; with r=R) in the presence of a catalyst (cat) to yield the cyclosiloxane of Formula I is illustrated in FIG. 1.

In various embodiments of the above described method for the synthesis of cyclosiloxanes of Formula I, in the cyclosiloxane of Formula II m+n is 3, 4, 5 or 6, preferably 4. The cyclosiloxanes are thus preferably cyclotrisiloxanes, cyclotetrasiloxanes, cyclopentasiloxanes and cyclohexasiloxanes. In various embodiments, in the cyclosiloxanes of Formula II n is 1 and m is 2, 3, 4 or 5, preferably 3. The cyclosiloxanes are thus pentamethylcyclotrisiloxane (D$_2$D$^H$), heptamethylcyclotetrasiloxane (D$_3$D$^H$), nonamethylcyclopentasiloxane (D$_4$D$^H$) or undecamethylcyclohexasiloxane (D$_5$D$^H$), preferably heptamethylcyclotetrasiloxane (D$_3$D$^H$). By reacting these cyclosiloxanes with the functionalized acetylene of formula III in a hydrosilylation reaction, the respective functionalized cyclosiloxanes are obtained as a mixture of the Markovnikov and anti-Markovnikov isomers, with the ratio depending on the catalyst used. In the Markovnikov isomer, the hydrogen atom in the cyclosiloxane is replaced by —CH=CHR, while in the anti-Markovnikov isomer, the hydrogen atom is replaced by —CR=CH$_2$. This is exemplarily shown for D$_4$D$^H$ in FIG. 2, wherein the cyclosiloxane of Formula II (1) is reacted with the functionalized acetylene (2a-f; with r=R) to yield the Markovnikov isomer (3-8A) and the anti-Markovnikov isomer (3-8B).

In various embodiments, R is selected from the group consisting of H, unsubstituted or substituted phenyl, hydroxyalkyl, preferably —(CH$_2$)$_p$—OH or —(CR'OH)—CH$_3$, —(CH$_2$)$_p$—COOH, and —COO(CH$_2$)$_p$CH$_3$, with p being 0 or an integer from 1 to 10, preferably 2 or 3, and R' being unsubstituted C$_{1-4}$ alkyl. In various embodiments, the acetylene of formula III is selected from the compounds 2a-2f:

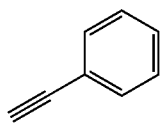
2a

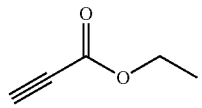
2b

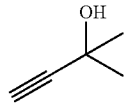
2d

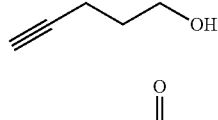
2c

2e

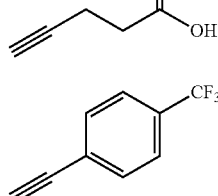
2f

Using these acetylene compounds 2a-2f in the above-described methods, with the cyclosiloxane of formula II being heptamethylcyclotetrasiloxane (D$_3$D$^H$) yields the following cyclosiloxanes of Formula I as Markovnikov (3-8A), anti-Markovnikov (3-8B) and mixed isomers (9a-9f):

(i) 2,2,4,4,6,6,8-heptamethyl-8-(1-phenylvinyl)-cyclotetrasiloxane (3B);
(ii) 2,2,4,4,6,6,8-heptamethyl-8-(2-phenylvinyl)-cyclotetrasiloxane (3A);
(iii) ethyl 2-(2,4,4,6,6,8,8-heptamethyl-cyclotetrasiloxan-2-yl)acrylate (4B);
(iv) ethyl 3-(2,4,4,6,6,8,8-heptamethyl-cyclotetrasiloxan-2-yl)prop-2-enoate (4A);
(v) 4-(2,4,4,6,6,8,8-heptamethyl-cyclotetrasiloxan-2-yl)pent-4-en-1-ol (5B);
(vi) 5-(2,4,4,6,6,8,8-heptamethyl-cyclotetrasiloxan-2-yl)pent-4-en-1-ol (5A);
(vii) 3-(2,4,4,6,6,8,8-heptamethyl-cyclotetrasiloxan-2-yl)-2-methylbut-3-en-2-ol (6B);
(viii) 4-(2,4,4,6,6,8,8-heptamethyl-cyclotetrasiloxan-2-yl)-2-methylbut-3-en-2-ol (6A);
(ix) 4-(2,4,4,6,6,8,8-heptamethyl-cyclotetrasiloxan-2-yl)pent-4-enoic acid (7B);
(x) 5-(2,4,4,6,6,8,8-heptamethyl-cyclotetrasiloxan-2-yl)pent-4-enoic acid (7A);
(xi) 2,2,4,4,6,6,8-heptamethyl-8-(1-(4-(trifluoromethyl)phenyl)vinyl)-cyclotetrasilxane (8B);
(xii) 2,2,4,4,6,6,8-heptamethyl-8-(2-(4-(trifluoromethyl)phenyl)vinyl)-cyclotetrasiloxane (8A);
(xiii) 2,4,6,8-tetramethyl-2,4,6,8-tetrakis(1-phenylvinyl)-cyclotetrasiloxane (9a);
(xiv) (E/Z)-2,4,6,8-tetramethyl-2,4,6-tris(1-phenylvinyl)-8-styryl-cyclotetrasiloxane (9b);
(xv) 2,4,6,8-tetramethyl-2,6-bis(1-phenylvinyl)-4,8-di((E/Z)-styryl)-cyclotetrasiloxane (9c);
(xvi) 2,4,6,8-tetramethyl-2,4-bis(1-phenylvinyl)-6,8-di((E/Z)-styryl)-cyclotetrasiloxane (9d);
(xvii) 2,4,6,8-tetramethyl-2-(1-phenylvinyl)-4,6,8-tri((E/Z)-styryl)-cyclotetrasiloxane (9e); or
(xviii) 2,4,6,8-tetramethyl-2,4,6,8-tetra((E/Z)-styryl)-cyclotetrasiloxane (9f).

The structures of the above compounds are also shown in FIGS. 3 and 4.

The hydrosilylation catalyst may be selected from the group consisting of platinum (Pt)-, rhodium (Rh)- or iridium (Ir)-containing catalysts. In preferred embodiments, the catalyst is a Pt-containing catalysts, optionally of the formula $PtL_q$, wherein q is an integer from 1 to 6 and L is a neutral organic ligand, preferably a phosphine, such as triphenylphosphine, or an olefin, such as 1,1,3,3-tetramethyl-1,3-divinyldisiloxane or 2,4,6,8-tetramethyldisiloxane-2,4,6,8-tetravinyltetrasiloxane, or an inorganic support, preferably charcoal, silica or alumina. Particularly desirable catalysts for the method of preparing a cyclosiloxane of formula I are platinum(0)-1,3-divinyl-1,1,3,3-tetramethyldisiloxane (Karstedt catalyst), tetrakistriphenylphosphine platinum(0), platinum on activated charcoal and platinum on alumina.

In the methods of preparing a biscyclosiloxane of Formula IV or V, an optionally functionalized vinyl cyclosiloxane of formula I, preferably the Markovnikov isomer, such as that of formula 3-8A where R is preferably hydrogen, is reacted with a cyclosiloxane of formula II, preferably $D_3D^H$, to yield a biscyclosiloxane connected by a carbon-carbon bridge (—$CH_2$—CH(R)— or —CH($CH_2$—R)—). Alternatively, the anti-Markovnikov isomer, such as that of formula 3-8B where R is preferably hydrogen, may be used. The reaction schemes for this reaction are schematically shown in FIG. 5A-C.

In various embodiments of this method of preparing a biscyclosiloxane, the acetylene is not functionalized, i.e. R is hydrogen, and the starting cyclosiloxane $D_3D^H$, so that the thus produced biscyclosiloxane is a biscyclosiloxane of formula VI

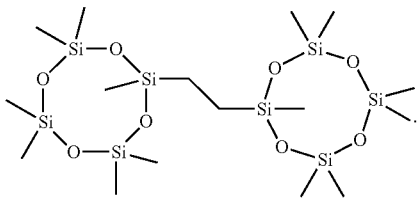

(VI)

This biscyclosiloxane is also herein referred to as bis(heptamethylcyclotetrasiloxanyl)-ethane (bis-$D_4$) and is a preferred embodiment of the described method. To prepare it, in a first step heptamethylcyclotetrasiloxane is reacted with acetylene in the presence of a hydrosilylation catalyst, as defined above. The resulting vinyl-functionalized cyclosiloxane is then reacted with freshly added heptamethylcyclotetrasiloxane to yield the above biscyclosiloxane of formula VI.

While for the preparation of the biscyclosiloxanes the same catalysts as described above can be used, in preferred embodiments the employed catalyst is selected from the group consisting of platinum(0)-1,3-divinyl-1,1,3,3-tetramethyldisiloxane (Karstedt catalyst), tetrakistriphenylphosphine platinum(0), and platinum on activated charcoal.

The reaction conditions are not particularly limited and reaction temperatures and times can be determined by those skilled in the art by routine experimentation. However, in preferred embodiments, the reaction is carried out at a temperature in the range of from about 30 to about 150° C., preferably 40 to 60° C. The reaction time may range from about 1 to about 48 hours, but is preferably 18 to 32 hours.

"About", as used herein, relates to ±20%, preferably ±10% of the numerical value to which it refers. "About 30" thus relates to 30±6, preferably 30±3.

Generally, the catalysts described herein can be used in concentrations of between about 0.0001 and about 1 mol-% based on the total amount of the cyclosiloxane educt(s). A preferred concentration range is from about 0.001 to about 0.1 mol-%, more preferably about 0.01 mol-%.

The reaction may be carried out in any suitable organic solvent. One example for such a suitable solvent is, without limitation, toluene. The reaction is typically carried out under inert atmosphere, preferably argon atmosphere.

To isolate and/or purify the product, the described methods can further comprises the step of removing the catalyst after the reaction is completed, preferably by filtration optionally over silica. The filtrate may subsequently be washed once or multiple times with an organic solvent, including but not limited to toluene and ethanol. The solvent may later be removed, for example by rotary evaporation. The thus obtained residue may additionally be dried under vacuum, for example by use of a vacuum pump.

The present invention also encompasses the cyclosiloxanes obtainable by the described processes. The functionalized cyclosiloxanes may be used as silane coupling agents and can be used in ring opening polymerization to obtain functionalized polydimethylsiloxane polymers. The functional groups can be used as anchoring points for the grafting of other polymer chains, thus yielding grafted copolymers, or to modify chemical, physical or rheological properties of the polymers.

In the following, the invention is described in greater detail by reference to concrete embodiments. It is however understood that the present invention is not limited to such embodiments, but may easily be adapted to use other cyclosiloxane educts and catalysts.

Such alternative embodiments are also encompassed by the scope of the present invention.

EXAMPLES

Example 1

Figure 1:
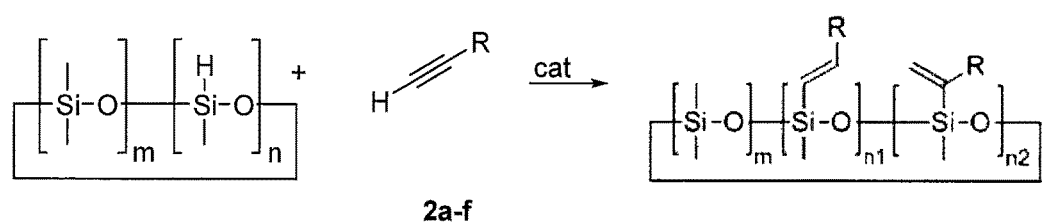
FIG. 1 illustrates a reaction scheme for the reaction of the cyclosiloxane of Formula II with the functionalized acetylene of Formula III (2a-f; with r=R) in the presence of a catalyst (cat) to yield the cyclosiloxane of Formula I.
Figure 2:
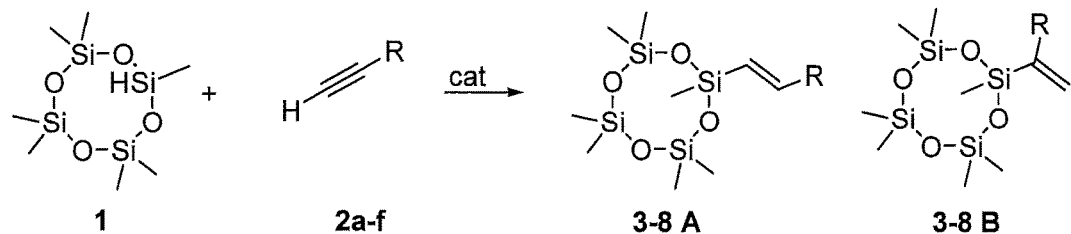
FIG. 2 illustrates an exemplary reaction wherein the cyclosiloxane of Formula II (1) is reacted with the functionalized acetylene (2a-f; with r=R) to yield the Markovnikov isomer (3-8A) and the anti-Markovnikov isomer (3-8B).
Figure 3:
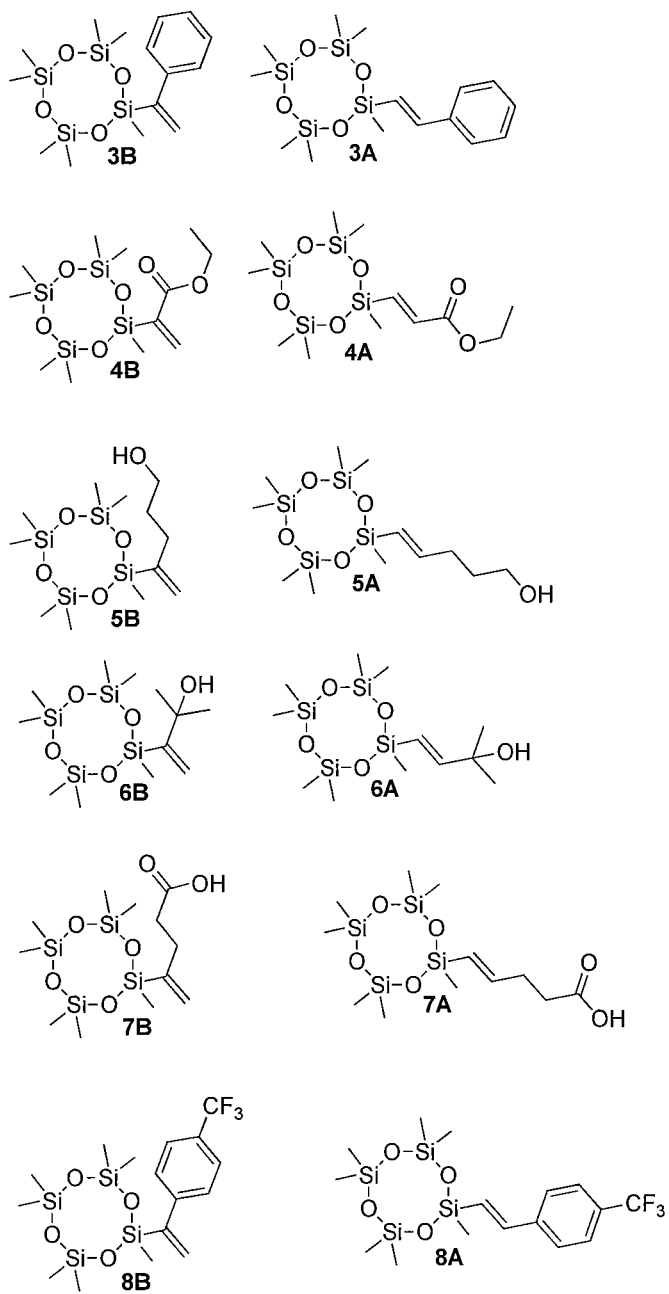
FIG. 3 shows structures for some compounds disclosed herein.
Figure 4:
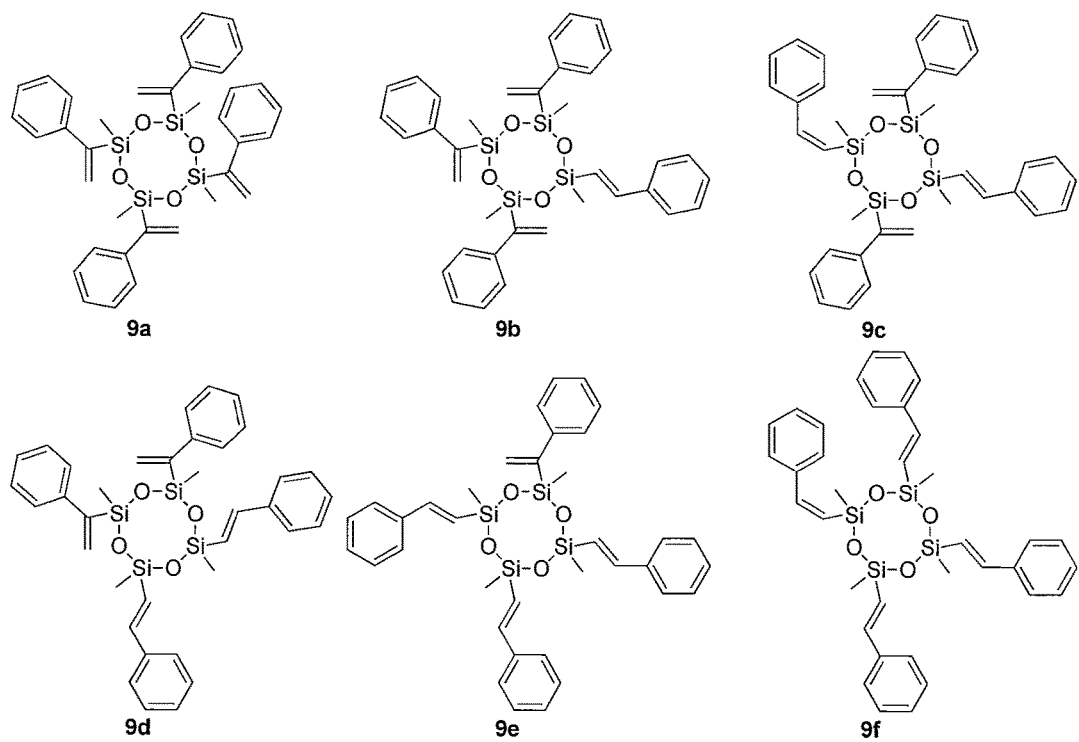
FIG. 4 shows structures for some compounds disclosed herein.
Figure 5A:
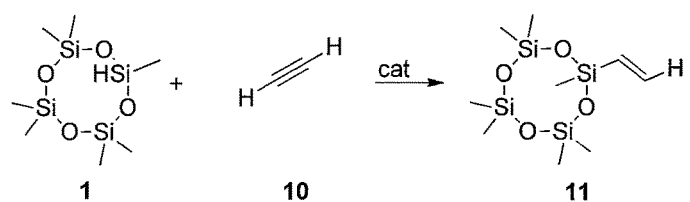
FIGS. 5A-5C illustrate some reaction schemes for preparing a biscyclosiloxane wherein the anti-Markovnikov isomer is used.
Figure 5B:
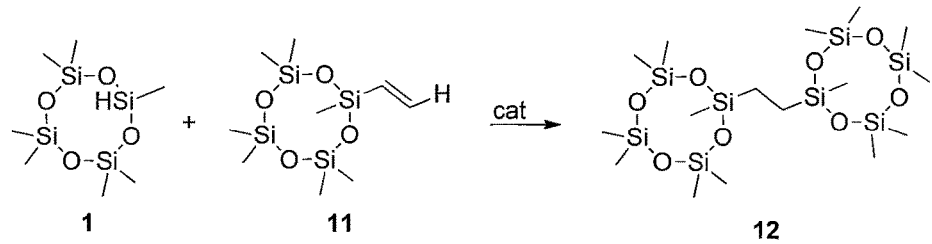
Figure 5C:
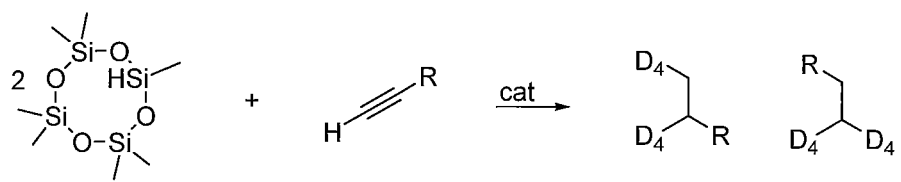

Synthesis of 2,2,4,4,6,6,8-heptamethyl-8-(1-phenylvinyl)-cyclotetrasiloxane (3B) and 2,2,4,4,6,6,8-heptamethyl-8-(2-phenylvinyl)-cyclotetrasiloxane (3A)

In a Schlenk flask under argon atmosphere, 0.2 g (1.77 mmol) of phenyl acetylene (2a) and 0.5 g (1.77 mmol) of heptamethylcyclotetrasiloxane (1) are added to 15 ml toluene. To this solution 0.01 mol % of a Pt-based catalyst, as defined in the below Table, is given. The mixture is stirred for 24 h at 40° C. Subsequently, the solution is purified by filtration over silica and washed with 20 ml toluene and ~30 ml ethanol. Both solvents are removed by rotary evaporation and the obtained residue is additionally dried by vacuum pump. The obtained product, a mixture of the corresponding Markovnikov (3A) and anti-Markovnikov (3B) isomers, gives, when Karstedt's catalyst (Platinum (0)-1,3-divinyl-1,1,3,3-tetramethyldisiloxane complex solution) is used, an isolated yield of >99%. In this particular case, a ratio of Markovnikov (3A) to anti-Markovnikov (3B) product of 1:0.4 is obtained.

An analogous procedure is applied using various catalysts, giving different yields and selectivities (see Table 1 below)

TABLE 1

| 2a n [mmol] | 1 n [mmol] | catalyst 0.01 mol-% | temperature [° C.] | isol. Yield (3A/3B) | ratio (A):(B) |
|---|---|---|---|---|---|
| 1.77 | 1.77 | Karstedt | 40 | quantitative | 1:0.4 |
| 1.77 | 1.77 | Pt on carbon | 40 | 71 | 1:0.5 |
| 1.77 | 1.77 | Pt on carbon | 80 | 70 | 1:0.5 |
| 1.77 | 1.77 | Pt on alumina | 40 | 77 | 1:0.5 |
| 1.77 | 1.77 | Tetrakistriphenyl phosphine platinum | 40 | 40 | 1:0.1 |

Example 2

Synthesis of ethyl 2-(2,4,4,6,6,8,8-heptamethyl-cyclotetrasiloxan-2-yl)acrylate (4B) and ethyl 3-(2,4,4,6,6,8,8-heptamethyl-cyclotetrasiloxan-2-yl)prop-2-enoate (4A)

In a Schlenk flask under argon atmosphere, 0.14 g (1.77 mmol) of ethylpropionate (2b) and 0.5 g (1.77 mmol) of heptamethylcyclotetrasiloxane (1) are added to 15 ml toluene. To this solution 0.01 mol % of a Pt-based catalyst, as defined in the Table below, is given. The mixture is stirred for 24 h at 40° C. Subsequently, the solution is purified by filtration over silica and washed with 20 ml toluene and ~30 ml ethanol. Both solvents are removed by rotary evaporation and the obtained residue is additionally dried by vacuum pump. The obtained product, a mixture of the corresponding Markovnikov (4A) and anti-Markovnikov (4B) isomers, gives an isolated yield of >99% when Karstedt's catalyst was used. In that case, the ratio of Markovnikov to anti-Markovnikov product is 0.5 to 1.

An analogous procedure is applied using various catalysts, giving different yields and selectivities (see Table 2 below)

TABLE 2

| 2b n [mmol] | 1 n [mmol] | catalyst 0.01 mol % | temperature [° C.] | isol. Yield (4A/4B) | ratio (A):(B) |
|---|---|---|---|---|---|
| 1.77 | 1.77 | Karstedt | 40 | quantitative | 0.5:1 |
| 1.77 | 1.77 | Pt on carbon | 40 | 2 | 1.1:1 |
| 1.77 | 1.77 | Pt on carbon | 60 | 21 | 1.10:1 |
| 1.77 | 1.77 | Pt on carbon | 80 | 50 | 1.1:1 |
| 1.77 | 1.77 | Pt on alumina | 40 | 2 | 1.1:1 |
| 1.77 | 1.77 | Tetrakistriphenyl phosphine platinum | 40 | 14 | 1.1:1 |

Example 3

Synthesis of bis(heptamethylcyclotetrasiloxanyl)-ethane (bis-D4) (12)

In a double-walled glass reactor under argon atmosphere 0.5 g (1.77 mmol) of heptamethylcyclotetrasiloxane (1) are added to 15 ml toluene. To this solution 0.01 mol % of a Pt-based catalyst, as defined in the below Table, is given. Acetylene is bubbled through the solution. The mixture is stirred for 24 h at 40° C. The intermediate product heptamethyl-8-vinyl-cyclotetrasiloxane (11) was isolated in order to determine the yield of the first step (up to 80% when Karsted's catalyst is used). An equimolar amount of heptamethylcyclotetrasiloxane and 0.01 mol % of a Pt-based catalyst, as defined in the below Table, dissolved in ~20 ml toluene were added to a solution of 11 (also in toluene) and stirred about 24 h and 40° C. Subsequently, the solution is purified by filtration over silica and washed with 20 ml of toluene and ~30 ml of ethanol. Both solvents are removed by rotary evaporation and the obtained residue is recrystallized in methanol at 4° C. The product (12) is obtained as white crystals with an isolated yield of 87% when Karsted's catalyst is used.

An analogous procedure is applied using various catalysts, giving different yields and selectivities (see Table 3 below)

TABLE 3

| acetylene n [mmol] | 1 n [mmol] | catalyst 0.01 mol % | temperature [° C.] | isol. Yield (11) |
|---|---|---|---|---|
| excess | 1.59 | Karstedt | 40 | 87 |
| | 26.00 | Karstedt | 40 | 90 |
| | 1.77 | Pt on carbon | 40 | 15 |

Example 4

2,4,6,8-tetramethyl-2,4,6,8-tetra((E)-styryl)-cyclotetrasiloxane (9)

In a Schlenk flask under argon atmosphere, 0.84 g (8.32 mmol) of phenyl acetylene (2a) and 0.5 g (2.08 mmol) of 2,4,6,8-tetramethyl-cyclotetrasiloxane are added to 15 ml toluene. To this solution 0.01 mol % of a Pt-based catalyst, as defined in the below Table, is given. The mixture is stirred for 24 h at 40° C. Subsequently, the solution is purified by filtration over silica and washed with 20 ml toluene and ~30 ml ethanol. Both solvents are removed by rotary evaporation and the obtained residue is additionally dried by vacuum pump. The obtained product (9), a mixture of the corresponding Markovnikov and anti-Markovnikov isomers, giving an isolated yield of 90% when Karsted's catalyst is used.

An analogous procedure is applied using various catalysts, giving different yields and selectivities (see Table 4 below)

TABLE 4

| 2a n [mmol] | 13 n [mmol] | catalyst 0.01 mol % | temperature [° C.] | isol. Yield (13) |
|---|---|---|---|---|
| 8.32 | 2.08 | Karstedt | 40 | 90 |
| 8.32 | 2.08 | Pt on carbon | 40 | 49 |
| 8.32 | 2.08 | Pt on carbon | 80 | 76 |

The invention claimed is:
1. A method of preparing a cyclosiloxane of Formula I,

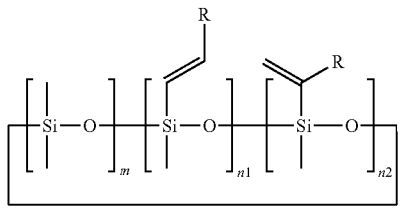 (I)

wherein
- each R is independently selected from the group consisting of hydrogen and an organic functionality selected from the group consisting of substituted or unsubstituted $C_{1-28}$ alkyl, $C_{2-28}$ alkenyl, $C_{2-22}$ alkynyl, $C_{3-12}$ cycloalkyl, $C_{3-12}$ cycloalkenyl, $C_{6-20}$ aryl, $C_{3-20}$ heteroaryl, $C_{7-9}$ aralkyl or alkylaryl, $C_{1-20}$ heteroalkyl, $C_{1-20}$ heterocyclyl with 1 to 5 ring heteroatoms selected from N, O and S, halogen, cyano, nitro, $-OR^1$, $-C(O)R^1$, $-C(O)OR^1$, $-OC(O)R^1$, $-NR^1R^2$, $-C(O)NR^1R^2$, $-NR^2C(O)R^1$, and $-Si(R^1)_o(OR^2)_{3-o}$;
- $R^1$ and $R^2$ are independently selected from the group consisting of hydrogen and $C_{1-28}$ alkyl, $C_{2-28}$ alkenyl, $C_{2-22}$ alkynyl, $C_{3-12}$ cycloalkyl, $C_{3-12}$ cycloalkenyl, $C_{6-20}$ aryl, $C_{3-20}$ heteroaryl, with 1 to 5 ring heteroatoms selected from N, O and S, $C_{7-9}$ aralkyl or alkylaryl, $C_{1-20}$ heteroalkyl, with 1 to 5 heteroatoms selected from N, O, halogen and S, $C_{1-20}$ heterocyclyl with 1 to 5 ring heteroatoms selected from N, O and S;
- each of m, n1 and n2 is 0 or an integer independently selected from 1 to 10, with m+n1+n2=3 to 10 and provided that not both of n1 and n2 are 0; and
- o is 0, 1, 2, or 3;

the method comprising:
reacting (i) a cyclosiloxane of Formula II

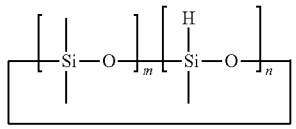 (II)

wherein m is as defined above and n=n1+n2;
with (ii) a substituted acetylene of Formula III

 (III)

wherein R is as defined above in the presence of a hydrosilylation catalyst to form the cyclosiloxane of Formula I.

2. The method according to claim 1, wherein in Formula II m+n=3, 4, 5 or 6.

3. The method according to claim 1, wherein in Formula II n is 1 and m is 3.

4. The method according to claim 1, wherein R is selected from the group consisting of H, unsubstituted or substituted phenyl, hydroxyalkyl and R' being unsubstituted $C_{1-4}$ alkyl.

5. The method according to claim 1, wherein R is selected from the group consisting of H, unsubstituted or substituted phenyl, $-(CH_2)_p-OH$, $-(CR'OH)-CH_3$, $-(CH_2)_p-COOH$ and
$-COO(CH_2)_pCH_3$, with p being 0 or an integer from 1 to 10, and R' being unsubstituted $C_{1-4}$ alkyl.

6. The method according to claim 1, wherein the cyclosiloxane of Formula I is
(i) 2,2,4,4,6,6,8-heptamethyl-8-(1-phenylvinyl)-cyclotetrasiloxane (3B);
(ii) 2,2,4,4,6,6,8-heptamethyl-8-(2-phenylvinyl)-cyclotetrasiloxane (3A);
(iii) ethyl 2-(2,4,4,6,6,8,8-heptamethyl-cyclotetrasiloxan-2-yl)acrylate (4B);
(iv) ethyl 3-(2,4,4,6,6,8,8-heptamethyl-cyclotetrasiloxan-2-yl)prop-2-enoate (4A);
(v) 4-(2,4,4,6,6,8,8-heptamethyl-cyclotetrasiloxan-2-yl)pent-4-en-1-ol (5B);
(vi) 5-(2,4,4,6,6,8,8-heptamethyl-cyclotetrasiloxan-2-yl)pent-4-en-1-ol (5A);
(vii) 3-(2,4,4,6,6,8,8-heptamethyl-cyclotetrasiloxan-2-yl)-2-methylbut-3-en-2-ol (6B);
(viii) 4-(2,4,4,6,6,8,8-heptamethyl-cyclotetrasiloxan-2-yl)-2-methylbut-3-en-2-ol (6A);
(ix) 4-(2,4,4,6,6,8,8-heptamethyl-cyclotetrasiloxan-2-yl)pent-4-enoic acid (7B);
(x) 5-(2,4,4,6,6,8,8-heptamethyl-cyclotetrasiloxan-2-yl)pent-4-enoic acid (7A);
(xi) 2,2,4,4,6,6,8-heptamethyl-8-(1-(4-(trifluoromethyl)phenyl)vinyl)-cyclotetrasiloxane (8B);
(xii) 2,2,4,4,6,6,8-heptamethyl-8-(2-(4-(trifluoromethyl)phenyl)vinyl)-cyclotetrasiloxane (8A);
(xiii) 2,4,6,8-tetramethyl-2,4,6,8-tetrakis(1-phenylvinyl)-cyclotetrasiloxane (9a);
(xiv) (E/Z)-2,4,6,8-tetramethyl-2,4,6-tris(1-phenylvinyl)-8-styryl-cyclotetrasiloxane (9b);
(xv) 2,4,6,8-tetramethyl-2,6-bis(1-phenylvinyl)-4,8-di((E/Z)-styryl)-cyclotetrasiloxane (9c);
(xvi) 2,4,6,8-tetramethyl-2,4-bis(1-phenylvinyl)-6,8-di((E/Z)-styryl)-cyclotetrasiloxane (9d);
(xvii) 2,4,6,8-tetramethyl-2-(1-phenylvinyl)-4,6,8-tri((E/Z)-styryl)-cyclotetrasiloxane (9e); or
(xviii) 2,4,6,8-tetramethyl-2,4,6,8-tetra((E/Z)-styryl)-cyclotetrasiloxane (9f).

7. The method according to claim 1, wherein the hydrosilylation catalyst is selected from the group consisting of platinum (Pt)-, rhodium (Rh)- or iridium (Ir)-containing catalysts.

8. The method according to claim 1, wherein the hydrosilylation catalyst is selected from Pt-containing catalysts of the formula $PtL_q$, wherein q is an integer from 1 to 6 and L is a neutral organic ligand or an inorganic support.

9. The method according to claim 1, wherein the hydrosilylation catalyst is selected from Pt-containing catalysts of the formula $PtL_q$, wherein q is an integer from 1 to 6 and L is a phosphine or an olefin or an inorganic support selected from at least one of charcoal, silica or alumina.

10. The method of claim 1, wherein the hydrosilylation catalyst is selected from the group consisting of platinum (0)-1,3-divinyl-1,1,3,3-tetramethyldisiloxane, tetrakistriphenylphosphine platinum(0), platinum on activated charcoal and platinum on alumina.

11. The method of claim 1, wherein each R is independently selected from the group consisting of hydrogen and an organic functionality selected from the group consisting of substituted or unsubstituted $C_{1-28}$ alkyl, $C_{2-28}$ alkenyl, $C_{2-22}$ alkynyl, $C_{3-12}$ cycloalkyl, $C_{3-12}$ cycloalkenyl, $C_{6-20}$ aryl, $C_{7-9}$ aralkyl or alkylaryl, $C_{1-20}$ heteroalkyl with 1 to 5 heteroatoms selected from N, O, halogen and S, $C_{1-20}$ heterocyclyl with 1 to 5 ring heteroatoms selected from N, O and S, halogen, cyano, nitro, —$OR^1$, —$C(O)R^1$, —$C(O)OR^1$, —$OC(O)R^1$, —$NR^1R^2$, —$C(O)NR^1R^2$, —$NR^2C(O)R^1$, and —$Si(R^1)_o(OR^2)_{3-o}$;

$R^1$ and $R^2$ are independently selected from the group consisting of hydrogen and $C_{1-28}$ alkyl, $C_{2-28}$ alkenyl, $C_{2-22}$ alkynyl, $C_{3-12}$ cycloalkyl, $C_{3-12}$ cycloalkenyl, $C_{6-20}$ aryl, $C_{3-20}$ heteroaryl with 1 to 5 ring heteroatoms selected from N, O and S, $C_{7-9}$ aralkyl or alkylaryl, $C_{1-20}$ heteroalkyl with 1 to 5 heteroatoms selected from N, O, halogen and S, $C_{1-20}$ heterocyclyl with 1 to 5 ring heteroatoms selected from N, O and S.

12. The method according to claim 1, wherein:
(i) the reaction is carried out at a temperature in the range of from 30 to 150° C.; and/or
(ii) the reaction time is 1 to 48 hours; and/or
(iii) the concentration of the hydrosilylation catalyst is between about 0.0001 and 1 mol-% based on the total amount of the cyclosiloxane educt(s); and/or
(iv) the reaction is carried out in a suitable organic solvent; and/or
(v) the reaction is carried out under inert atmosphere.

* * * * *

UNITED STATES PATENT AND TRADEMARK OFFICE
CERTIFICATE OF CORRECTION

PATENT NO. : 10,059,728 B2
APPLICATION NO. : 15/294920
DATED : August 28, 2018
INVENTOR(S) : David Briers et al.

It is certified that error appears in the above-identified patent and that said Letters Patent is hereby corrected as shown below:

In the Specification

Column 6, Line 53, change "cyclotetrasilxane" to -- cyclotetrasiloxane --.
Column 10, Line 15, change "Karsted's" to -- Karstedt's --.
Column 10, Line 24, change "Karsted's" to -- Karstedt's --.
Column 10, Line 55, change "Karsted's" to -- Karstedt's --.

In the Claims

Column 11, Line 30, change "with 1 to 5 ring" to -- preferably with 1 to 5 ring --.

Signed and Sealed this
Ninth Day of July, 2019

Andrei Iancu
*Director of the United States Patent and Trademark Office*